US012300394B1

(12) United States Patent
Safarzadeh (10) Patent No.: US 12,300,394 B1
(45) Date of Patent: May 13, 2025

(54) SYSTEM, METHOD AND APPARATUS FOR TWO-WAY LANGUAGE TRANSLATION IN A HEALTHCARE ENVIRONMENT (71) Applicant: Arvand Asad Safarzadeh, Houston, TX (US)

(72) Inventor: Arvand Asad Safarzadeh, Houston, TX (US)

(*) Notice: Subject to any disclaimer, the term of this patent is extended or adjusted under 35 U.S.C. 154(b) by 0 days.

(21) Appl. No.: 18/780,385

(22) Filed: Jul. 22, 2024

(51) Int. Cl.
*G06F 40/58* (2020.01)
*G16H 80/00* (2018.01)

(52) U.S. Cl.
CPC ............ *G16H 80/00* (2018.01); *G06F 40/58* (2020.01)

(58) Field of Classification Search
CPC ......... G06F 40/58; G06F 40/35; G06F 40/263
See application file for complete search history.

(56) References Cited

U.S. PATENT DOCUMENTS

| | | | |
|---|---|---|---|
| 5,854,997 A | 12/1998 | Sukeda et al. | |
| 6,339,410 B1 | 1/2002 | Milner et al. | |
| 7,716,037 B2 | 5/2010 | Precoda et al. | |
| 9,922,168 B2 | 3/2018 | Traughber et al. | |
| 2007/0239424 A1 | 10/2007 | Payn | |
| 2010/0250271 A1* | 9/2010 | Pearce | G06Q 10/06 705/2 |
| 2010/0287001 A1* | 11/2010 | Pearce | G06Q 10/06 235/375 |
| 2012/0245920 A1 | 9/2012 | Wu | |
| 2013/0079599 A1* | 3/2013 | Holmes | A61B 8/483 600/300 |
| 2013/0346098 A1* | 12/2013 | Denholm | G16H 40/20 705/2 |

(Continued)

FOREIGN PATENT DOCUMENTS

RU 2627927 C2 * 8/2017 ......... G01N 35/1065
WO 2022216739 A1 10/2022

OTHER PUBLICATIONS

Somers, H.L., et al.; A computer-based aid for communication between patients with limited English and their clinicians, using symbols and digitised speech, International Journal of Medical Informatics, vol. 77, Issue 8, 2008, pp. 507-517, ISSN 1386-5056, https://doi.org/10.1016/j.ijmedinf.2007.10.007. (https://www.sciencedirect.com/science/article/pii/S1386505607001773); Published by Elesevier Ireland Ltd. (2007).

*Primary Examiner* — Vijay B Chawan
(74) *Attorney, Agent, or Firm* — Lloyd & Mousilli; Benjamin M. Hanrahan (57) ABSTRACT

A healthcare translation apparatus, system, and method for two-way language translation in a healthcare environment is presented herein. The system includes a patient device in communication with a healthcare device, and a translation module configured to facilitate translation of inputs provided at the patient and healthcare devices. When a patient enters an input at the patient device, that input is sent to the translation module for real-time, translation into the language chosen by the healthcare provider. Similarly, when a health care provider enters an input through the healthcare device, that input is sent to the translation module for real-time, translation into the language chosen by the patient. Upon termination of the session, any and all data corresponding to the communication session is permanently deleted from the system and apparatus.

18 Claims, 6 Drawing Sheets

(56) References Cited

U.S. PATENT DOCUMENTS

| | | | |
|---|---|---|---|
| 2014/0170735 A1* | 6/2014 | Holmes | G01N 21/76 435/287.1 |
| 2016/0054343 A1* | 2/2016 | Holmes | G01N 35/026 422/65 |
| 2016/0320381 A1* | 11/2016 | Holmes | G01N 35/10 |
| 2021/0318348 A1* | 10/2021 | Holmes | G01N 35/04 |
| 2021/0335502 A1 | 10/2021 | Cordell et al. | |
| 2022/0170951 A1* | 6/2022 | Holmes | B01L 3/5027 |
| 2022/0246312 A1* | 8/2022 | Giovanis | G16H 10/20 |
| 2023/0289537 A1 | 9/2023 | D'Penha et al. | |

* cited by examiner

SYSTEM, METHOD AND APPARATUS FOR TWO-WAY LANGUAGE TRANSLATION IN A HEALTHCARE ENVIRONMENT

FIELD OF THE INVENTION

The present invention is generally directed to a system, method and apparatus for two-way, real-time language translation, and more specifically to a system, method and apparatus that provides real-time language (e.g., written or spoken) translation between a patient device and a healthcare device in a healthcare environment, such as in a pharmacy, hospital, emergency care facility, physician's office, etc.

BACKGROUND OF THE INVENTION

Many situations in the healthcare industry are often faced with a language barrier between the patient or customer and the healthcare provider, including, for example, but not limited to a pharmacist, physician, nurse, etc. For example, in the event the patient or customer does not speak, read or write English or otherwise does not speak, read or write the same language as the healthcare provider, communication between the patient and the healthcare provider is difficult, and in some cases, not possible. This is particularly important when the healthcare provider is attempting to communicate instructions or counseling to the patient.

As just an example, in a pharmacy setting where a patient is attempting to fill or receive a medication from a pharmacist, in many cases, the pharmacist or other pharmacy personnel must communicate detailed instructions and counseling to the patient regarding the medication, including how to store the medication, how to handle the medication, how to take or administer the medication, and other precautions, warnings, instructions, etc. relating to the medication. If there is a language barrier, and the patient is unable to clearly understand English or otherwise is unable to clearly understand the language of which the pharmacist is speaking, then the patient will not be able to understand the important instructions or counseling. Similarly, if the patient has questions or would like to communicate with the pharmacist or other healthcare provider or personnel, any language barrier would impede that communication.

There is thus a need in the art for a system, method and apparatus that can facilitate or otherwise provide real-time language translation between a patient and a healthcare provider in a healthcare environment. The proposed apparatus may include separate devices for the patient and healthcare provider, each in communication with one another and/or with a control device that includes a translation module for providing the real-time translation services.

SUMMARY OF THE INVENTION

Accordingly, the present invention is generally directed to a healthcare translation apparatus, a system, and a method for at least one-way, although more practically, two-way language translation between a patient and a healthcare provider or personnel in a healthcare environment. More specifically, the various embodiments of the present invention include a patient or customer device, operated or used by a patient or customer, in direct or indirect communication with a healthcare device, operated or used by a healthcare provider or personnel.

Furthermore, a communication session is initiated at the translation apparatus either by a patient or a healthcare provider in order to facilitate effective communication therebetween, often including, but not limited to patient counseling, providing and/or receiving instructions for the storage and use of a medication, etc.

In particular, both of the devices, e.g., the patient device and the healthcare device, include at least one input component or capability, such as, through a microphone, keyboard, touchscreen display, pointing device, etc. In at least one embodiment, the patient device may only need or include a microphone and the touchscreen display, whereas the healthcare device may also include a keyboard for allowing or for further facilitating typed inputs. Moreover, both of the devices, e.g., the patient device and the healthcare device, include at least one output component or capabilities, such as through one or more speakers, a display screen, etc.

The apparatus, system and method disclosed herein also includes a translation module that is configured to translate a patient input provided in a patient language (e.g., written or spoken) to a healthcare output (e.g., written or spoken) in a healthcare language, and to translate a healthcare input (e.g., written or spoken) in the healthcare language to a patient output (e.g., written or spoken) in the patient language. In other words, when a patient speaks into the corresponding microphone or otherwise enters a communication input, that input is sent to the translation module for real-time, accurate translation into the language chosen by or spoken by the healthcare provider. Similarly, when a health care provider speaks into the corresponding microphone, types on the keyboard or otherwise enters a communication input through the healthcare device, that input is sent to the translation module for real-time, accurate translation into the language chosen by the patient. The outputs, at either the patient side or the healthcare side can be in written text, spoken words or other forms, regardless of the manner or form of input.

Furthermore, the translation module may be disposed locally, for example, on the apparatus, control device, patient device and/or healthcare device, or remotely, for example, on a remote server or remote management system. In either case, the translation module may implement or use any one or more types of translation technologies, now known or later developed, including but in no way limited to machine translation (e.g., an automated system that translates text or speech from one language to another), neural machine translation (NMT) (e.g., using artificial neural networks to improve translation quality by understanding context of an input), statistical machine translation (SMT) (e.g., using models to learn translation patterns from data and applying those patterns to translate new inputs), hybrid machine translation (e.g., combining multiple machine translation techniques). In this manner, the translation module of at least one embodiment may utilize or include machine learning, large language models (LLM) and/or other types of artificial intelligence systems and/or techniques, whether integrated within the translation module or external thereto.

At the end of the session, or when both of the users (the patient and the healthcare provider) are finished communicating, the session may be terminated. Upon termination of the session, at least some, and in some cases, any and all data corresponding to the communication session, including, for example, the inputs provided by the patient device and/or healthcare device, the translations generated by the translation module, and in some cases, any patient-identifying information, including the patient's name, photos, voice, images, etc., are permanently deleted from the apparatus and system in compliance with any healthcare regulations or laws, including but not limited to the Health Insurance Portability and Accountability Act (HIPPA).

In some embodiments, and prior to deletion, a user (e.g., a patient or healthcare provider) may choose to retain a transcript of the communication session. In this manner, some embodiments may also include a printer capable or physically printing a written transcript of the communication session on a paper or other medium. Some embodiments will also or instead allow electronic communication of the transcript, for example, through e-mail or text message if desired.

BRIEF DESCRIPTION OF DRAWINGS

Like reference numerals refer to like parts throughout the several views of the drawings provided herein.

DETAILED DESCRIPTION OF THE INVENTION

Figure 1:
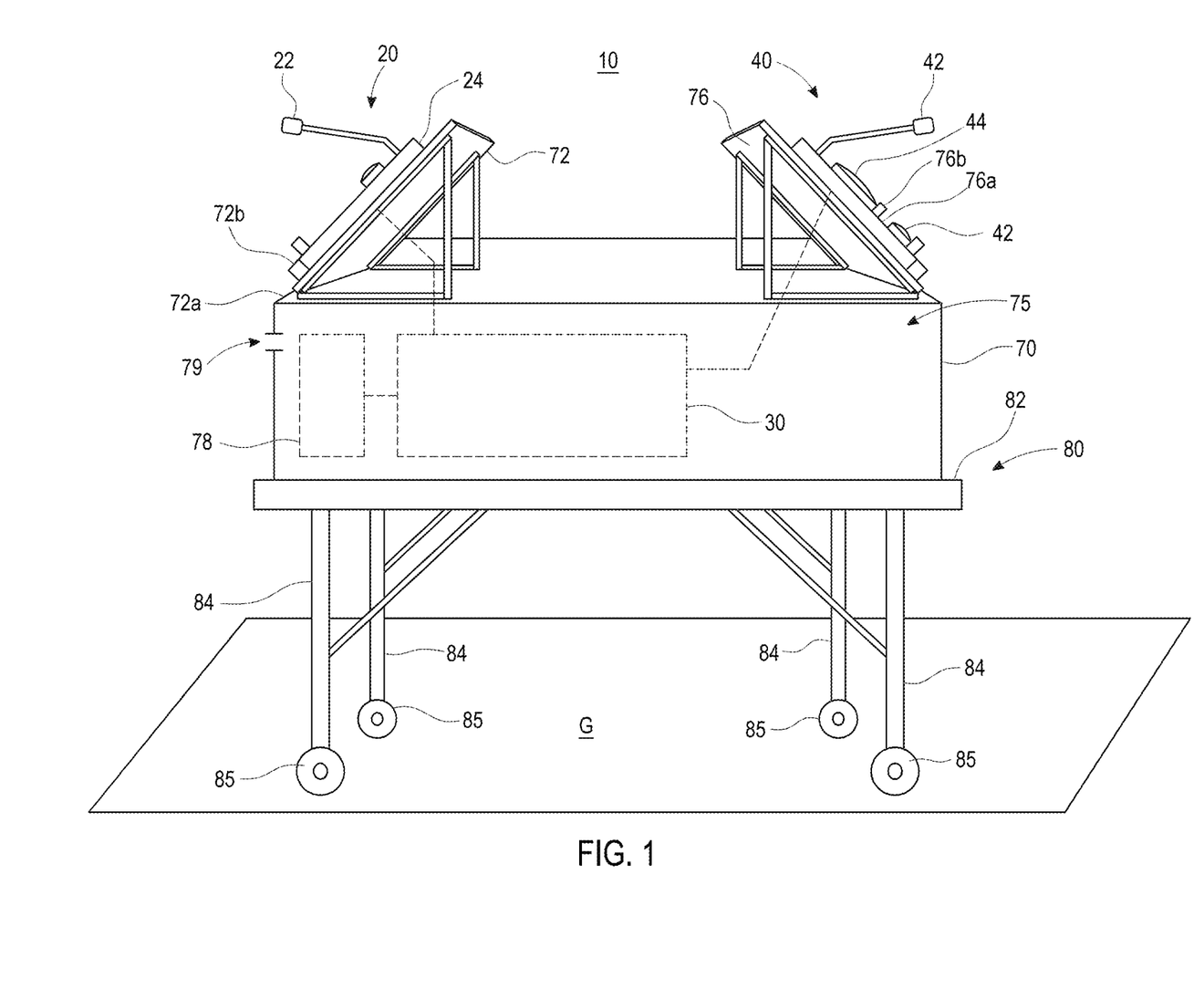
FIG. 1 is a side elevation view of the translation apparatus as disclosed in accordance with at least one embodiment of the present invention.
Figure 3:
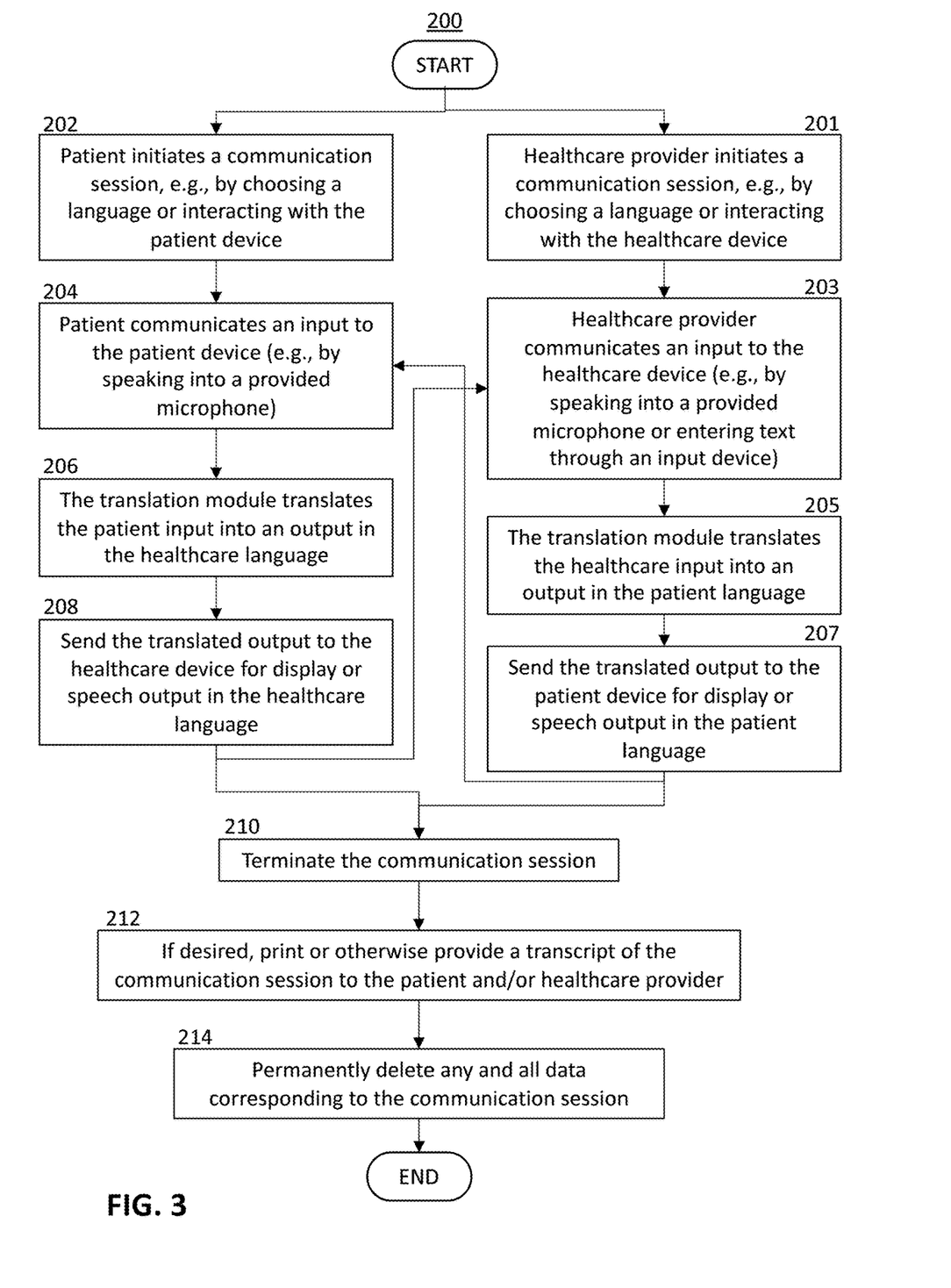
FIG. 3 is a high-level flow chart of the method for two-way language translation in a healthcare environment as disclosed in accordance with at least one embodiment of the present invention.
Figure 4:
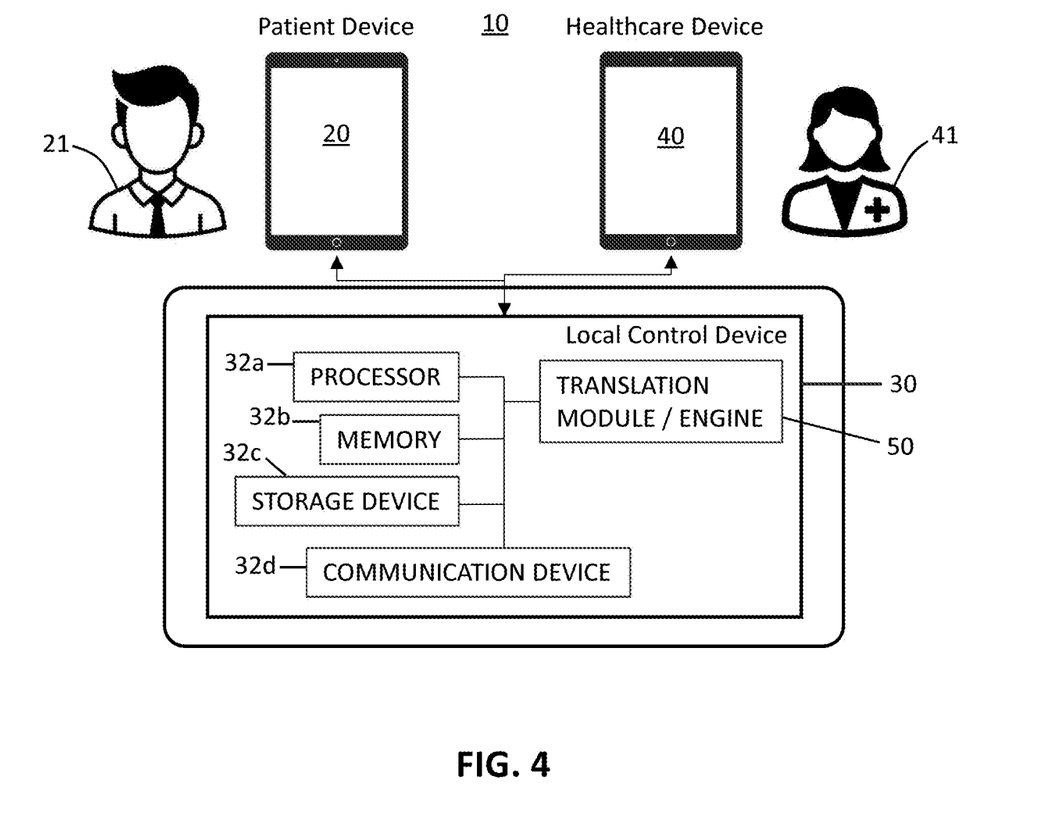
FIG. 4 is a schematic block diagram of the system for two-way language translation in a healthcare environment as disclosed in accordance with at least one embodiment of the present invention.

As shown in the accompanying drawings, and with particular reference to FIGS. 1, 3, and 4, the present invention is generally directed to an apparatus 10, a system 100 and a method 200 for two-way language translation in a healthcare environment. More specifically, the various embodiments of the present invention include a patient device 20, operated or used by a patient 21, in communication with a healthcare device 40, operated or used by a healthcare provider or personnel 41.

In general, and as described in more detail herein in connection with the various embodiments of the present invention, a user or patient 21 at the patient device 20 is able to communicate an input (e.g., via spoken words or audio, typed text, touchscreen or other selections of pre-generated communications, etc.) into the patient device 20, which is then translated, in real-time, and communicated to the healthcare provider 41 via the healthcare device 40 (e.g., via machine-translated text, machine-translated audio, images, etc.) Similarly, a user or healthcare provider 41 at the healthcare device 40 is able to communicate an input (e.g., via spoken words, audio, typed text, touchscreen or other selections of pre-generated communications, etc.) into the healthcare device 40, which is then translated, in real-time, and communicated to the patient 21 via the patient device 20 (e.g., via machine-translated text, machine-translated audio, images, etc.)

Figure 2A:
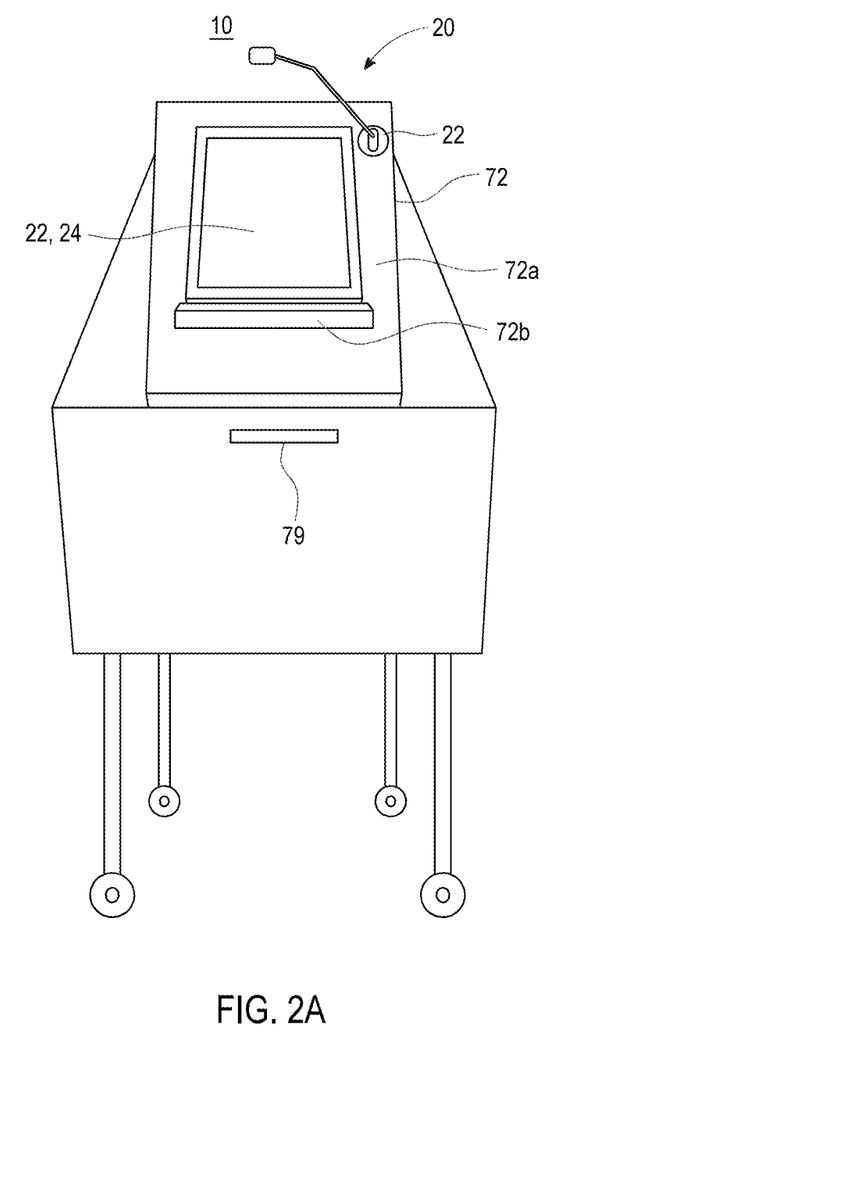
FIG. 2A is an end view of the translation apparatus illustrated in FIG. 1.

With reference now to FIGS. 1 and 2A, the patient device 20 of at least one embodiment of the present invention includes at least one patient input component or device 22 and at least one patient output component or device 24. For example, the patient input component 22 may include a microphone or other like device that is capable of receiving audio input from the patient (e.g., spoken words), and/or a pointing device, such as a computer mouse, touchpad, trackpad, trackball, stylus, touchscreen, etc. It should be noted that while FIGS. 1 and 2A illustrate a separate or external microphone, in other implementations or embodiments, the patient device 20 may include input and output components 22, 24 that are integrated within a single device or housing.

Figure 2B:
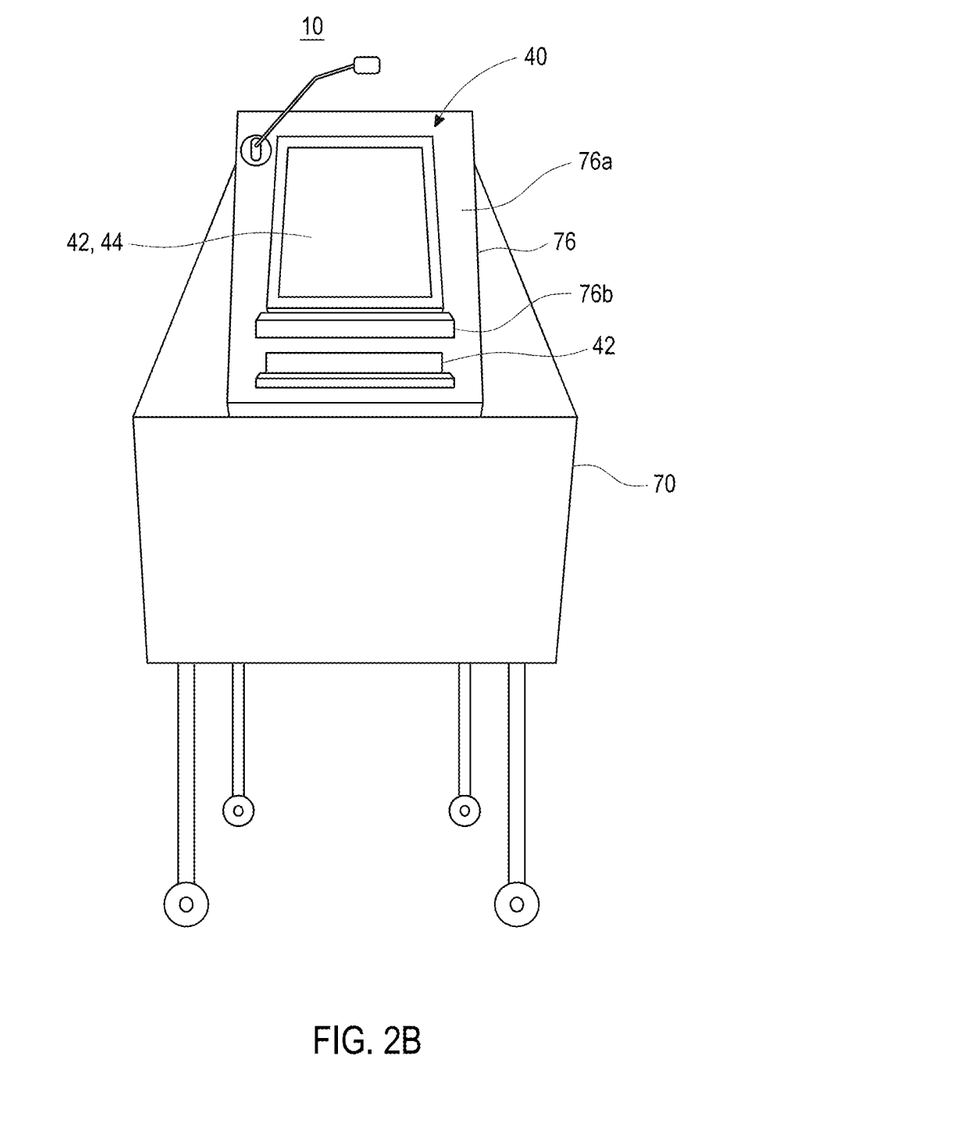
FIG. 2B is another end view of the translation apparatus illustrated in FIG. 1.

Furthermore, with reference to FIGS. 1 and 2B, the healthcare device 40 of at least one embodiment of the present invention includes at least one healthcare input component or device 42 and at least one healthcare output component or device 44. For example, the patient input component(s) 42 may include a microphone or other like device that is capable of receiving audio input from the patient (e.g., spoken words), a pointing device, such as a computer mouse, touchpad, trackpad, trackball, stylus, touchscreen, etc., and/or a keyboard or keypad. It should be noted that while FIGS. 1 and 2B illustrate some separate or external input/output devices, such as a separate or external microphone and keyboard, in other implementations or embodiments, the healthcare device 40 may include input and output components 42, 44 that are integrated within a single device or housing.

Figure 5:
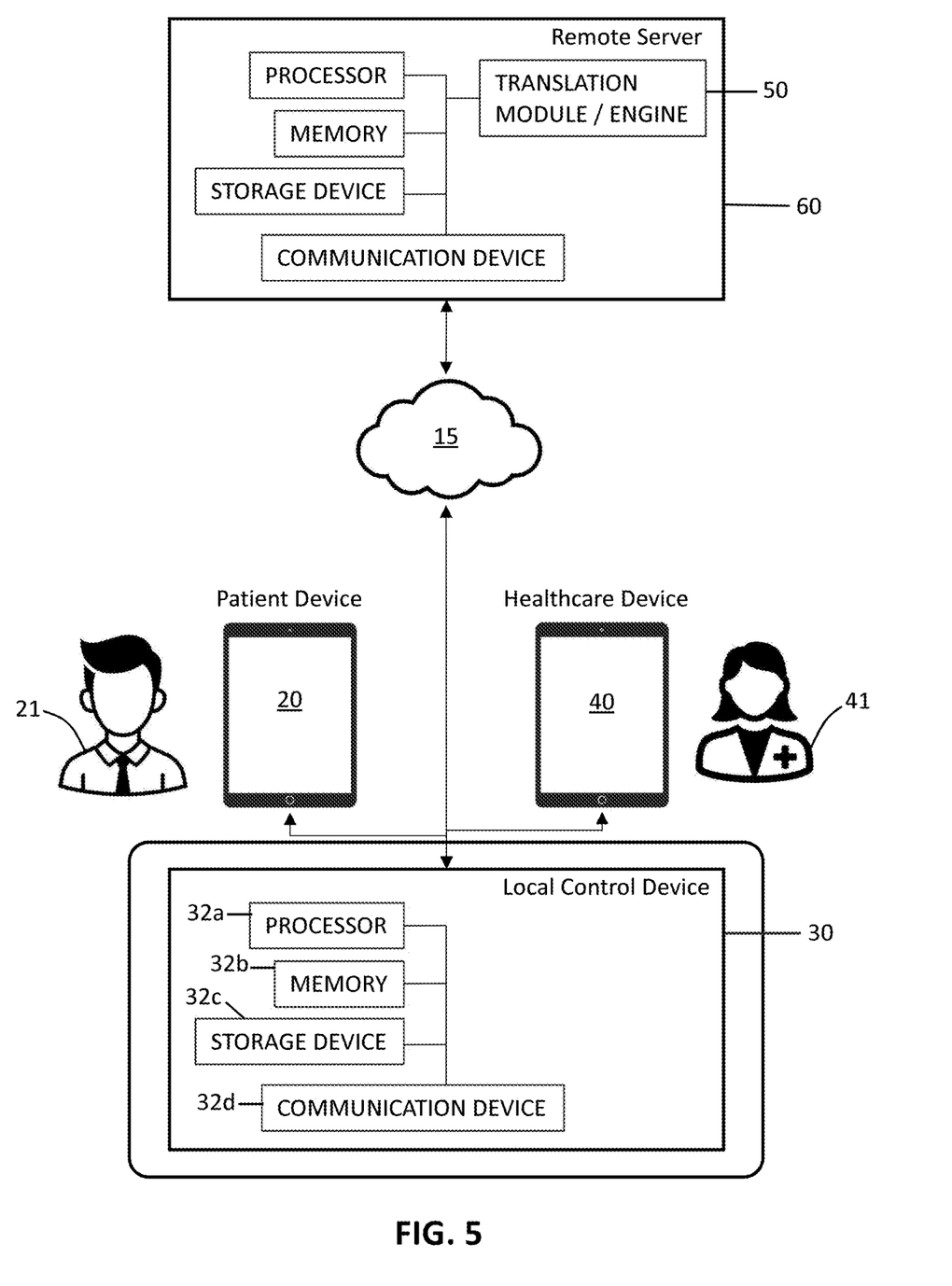
FIG. 5 is a schematic block diagram for two-way language translation in a healthcare environment as disclosed in accordance with another embodiment of the present invention.

Additionally, the various embodiments of the present invention include at least one translation module or engine, generally referenced as 50, for example, in FIGS. 4 and 5. As will be described further in accordance with other embodiments of the present invention, the one or more translation modules 50 may be disposed in one or more locations, for example, on or in one or both of the patient device 20 and healthcare device, on or in a local control device 30, and/or remotely on or in a remote management system 60. In either case, the translation module 50, of the various embodiments disclosed herein, is configured to receive an input (e.g., audio, text, etc.) in an originating language and translate the input to an output in a target language. The output is then communicated and displayed on the output device, e.g., the patient device 20 or the healthcare device 40. For instance, the translation module or engine 50 is configured to receive a patient input (e.g., an input from the patient device 20) provided in a patient's language, and translate that patient input into a healthcare language (e.g., a language that is selected by or understood by the healthcare provider). Similarly, the translation module or engine 50 is also configured to receive a healthcare input (e.g., an input from the healthcare device 40) provided in the healthcare's language, and translate that healthcare input into a patient language (e.g., a language that is selected by or understood by the patient).

More specifically, a patient input (e.g., spoken words, typed text, selected inputs, etc.) may be entered into the patient device 20 in a patient language, or otherwise in a language which the patient speaks and/or otherwise understands. That patient input is then communicated to the translation module or engine 50 which translates the patient input, in real-time, to a pre-defined healthcare language or target language. For instance, the healthcare language may be selected by the particular healthcare provider during each communication session or it may be preset as a default language. In any case, after the translation module 50 translates the patient input, the translated message or output is transmitted to the healthcare device 40 for output by the at least one healthcare output component 44, e.g., a display screen, speaker, etc.

Similarly, a healthcare input (e.g., spoken words, typed text, selected inputs, etc.) may be entered into the healthcare device 40 in a healthcare language, or otherwise in a language which the healthcare provider speaks and/or otherwise understands. That healthcare input is then communicated to the translation module or engine 50 which translates the healthcare input, in real-time, to a patient language or target language. For instance, as will be described herein, the patient language may be selected by the particular patient at the start of each communication session or it may automatically be detected by the system as the patient speaks, types or otherwise generates a patient input. In any case, after the translation module 50 translates the healthcare input into the patient language, the translated message or output is transmitted to the patient device 20 for output by the at least one patient output component 24, e.g., a display screen, speaker, etc.

In this manner, using the apparatus 10 of at least one embodiment, the patient 21 and healthcare provider 41 may communicate back-and-forth during a communication session through the real-time translation of the messages or inputs by the translation module 50.

When the communication session between the patient 21 and the healthcare provider 41 through the apparatus 10 has ended, as described herein below, any saved data corresponding to the communication session, including, for example, the inputs provided by the patient device 20 and/or healthcare device 40, the translations generated by the translation module 50, and in some cases, any patient-identifying information, including the patient's name, photos, voice, images, etc., are deleted from the apparatus 10 and system 100. More specifically, during the course of the communication sessions, certain information or data may be temporarily saved, e.g., input(s) provided by the patient and received by the patient device 20, input(s) provided by the healthcare provider and received by the healthcare device 40, translations generated by the translation module 50, identifications or names of medications, diagnoses, recommendations, instructions, etc., and in some cases, identifying information that may identify the patient, such as name, patient ID, etc. In some embodiments, all of that information will be deleted at the end of the communication session, in compliance with any healthcare regulations or laws, including but not limited to the Health Insurance Portability and Accountability Act (HIPPA).

Moreover, with reference to FIGS. 4 and 5, at least one embodiment of the present invention includes at least one local control device, generally referenced as 30. Although one local control device 30 is shown as being communicative with each of the patient device 20 and the healthcare device 40, in other embodiments, there may be two or more control devices, one connected to or as part of the patient device 20 and another connected to or as part of the healthcare device 40. In any case, the at least one control device 30 may include a computer processor or processing circuitry 32a, memory 32b, one or more data storage devices 32c, and one or more communication or network device(s) or interface(s) 32d. The processor or processing circuitry 32a may be coupled to the corresponding memory 32b, storage device 32c and network interface 32d to facilitate implementation of the present invention in the intended manner.

More in particular, the processor 32a or processing circuitry may be realized as one or more hardware logic components or circuits, such as, without limitation, one or more types of components that may include field programmable gate arrays (FPGAs), application specific integrated circuits (ASICs), application specific standard products (ASSPs), system-on-a-chip systems (SOCs), general purpose microprocessors, microcontrollers, digital signal processors (DSPs), or other like hardware components that can execute or implement computer instructions, software, etc., including, for example, the various features and components as described in accordance with at least one embodiment of the present invention and configured to implement or facilitate the implementation of the method 200 described herein. The processor 32a can execute instructions within the control device 30, including instructions stored in the memory 32b. Furthermore, the processor may provide, for example, for coordination of the other components or devices, including the patient device 20 and/or the input/output components 22, 24 thereof, the healthcare device 40 and/or the input/output components 42, 44 thereof, user interfaces, applications run by the control device 30, patient device 20 or healthcare device 40, and communication by, to or from control device 30.

The memory 32b of local control device 30 stores information within the device 30, and can be implemented as one or more of a computer-readable medium or media, a volatile memory unit or units, or a non-volatile memory unit or units, such as random access memory (RAM), read-only memory (ROM), flash memory, etc., or other like device(s) configured to implement the present invention in the intended manner, for example, by storing and assisting with the execution of one or more applications, modules, or components capable of implementing the system 100 and method 200 described herein. It should be noted that non-transitory computer readable media includes all computer-readable media except for a transitory, propagating signal.

The data storage device(s) 32c, as used herein, may include a hard disk drive, external drive, USB drive, solid state drive, virtual drive, could-based storage drive, or other types of volatile or non-volatile memory.

Moreover, the communication device 32d may include a network communication hardware/software component structured to facilitate communication between the control device 30 and other components or device of the system 10 or method 200, including, for example, the patient device 20, the healthcare device 40, or in some cases, remote management system or server 60.

More in particular, with reference to FIG. 4, in at least one embodiment, the translation module or engine 50 may be locally implemented or disposed on the control device(s) 30 such that all communications, inputs, outputs and translations provided and generated in accordance with at least one embodiment are maintained locally on the apparatus 10, itself. This can provide some assurances of security and privacy in that none of the inputs or communications are transmitted to a remote location for storage or processing. It should be noted that, in the local embodiment of the invention as just described, the control device(s) 30 and/or the patient device 20 and healthcare device 40 may have Internet access, for example, to provide software updates and/or routine maintenance of the apparatus.

However, in other embodiments, as shown in the schematic representation of FIG. 5, the system 100 may include one or more remote management systems 60, such as a web-based or cloud-based server or other like computing device disposed in a location that is remote from the apparatus 10, such that access to the server or remote system 60 or communication with the server or remote system 60 is facilitated through network 15. As an example, the network 15, as used herein, may include virtually any computer, communication or data network such as the World Wide Web, Internet, Intranet, Wide Area Network(s), Local Area Network(s), Metro Area Network(s), Telecommunication Network(s) (e.g., 3G, 4G, 5G, LTE), cellular or wired networks, etc., or any combination thereof.

The remote management device or system 60, as used herein, may include one or a series of computers that each include a computer processor or processing circuitry, memory, one or more data storage devices, and one or more communication or network device(s) or interface(s), that operate in a similar manner as that described above with regard to the control device 30.

Of note, however, in the embodiment schematically illustrated in FIG. 5, the translation module 50 is disposed in a remote location, e.g., as part of the server or management system 60. In this embodiment, the local control device 30 and/or the individual patient or healthcare devices 20, 40 may communicate with the remote management system 60 and/or translation module 60 in order for the system 100 or method 200 described herein to perform the translations.

In yet other embodiments, a hybrid or combined local/remote environment may be implemented such that some of the translations may occur or be generated locally (e.g., via a location translation module), while other translations may occur or be generated remotely (e.g., via a remote translation module).

In any event, the translation module 50 of the various embodiments, whether locally or remotely disposed relative to the apparatus 10, may be implemented in hardware and/or software and configured to translate inputs (whether text-based inputs, speech or audio inputs, etc.) to an output (e.g., whether a text-based output, speech or audio output, etc.) in a selected, defined, or pre-defined language. The translation module 50 may implement or use any one or more types of translation technologies, now known or later developed, including but in no way limited to machine translation (e.g., an automated system that translates text or speech from one language to another), neural machine translation (NMT) (e.g., using artificial neural networks to improve translation quality by understanding context of an input), statistical machine translation (SMT) (e.g., using models to learn translation patterns from data and applying those patterns to translate new inputs), hybrid machine translation (e.g., combining multiple machine translation techniques). In this manner, the translation module 50 of at least one embodiment may utilize or include machine learning, large language models (LLM) and/or other types of artificial intelligence systems and/or techniques, whether integrated within the translation module 50 or external thereto.

Referring again to FIGS. 1, 2A and 2B, the apparatus 10 of at least one embodiment further includes a main housing, generally referenced as 70 defining an interior portion 75 therein. IN at least one embodiment, the local control device 30 is disposed at least partially, and in some cases entirely, within the interior portion 75 of the housing 70.

Furthermore, the patient device 20 may be supported on or by a patient device support 72. More specifically, the patient device support 72 may, in at least one embodiment include a supporting surface 72a that supports at least a portion of the patient device 20, such as a display screen 24, thereon. For instance, in some cases, the display screen 24 or patient device 20 may be embedded or framed within the surface 72a such that the patient 21 is able to see the display screen and in some cases interact with the display screen, e.g., by providing touchscreen or other inputs thereon. In other cases, as shown, the surface 72a may include a ledge 72b upon which the display screen 24 or patient device 20 is maintained. Furthermore, in at least one embodiment, the patient device support 72, and in particular, the surface 72a thereof, may be angled relative to the ground, as shown in FIG. 1, for example.

Similarly, the healthcare device 40 may be supported on or by a healthcare device support 76. More specifically, the healthcare device support 76 may, in at least one embodiment include a supporting surface 76a that supports at least a portion of the healthcare device 40, such as a display screen 44, thereon. For instance, in some cases, the display screen 44 or healthcare device 40 may be embedded or framed within the surface 76a such that the healthcare provider or personnel 41 is able to see the display screen 44 and in some cases interact with the display screen 44, e.g., by providing touchscreen or other inputs thereon. In other cases, as shown, the surface 76a may include a ledge 76b upon which the display screen 44 or healthcare device 40 is maintained. Furthermore, in at least one embodiment, the healthcare device support 76, and in particular, the surface 76a thereof, may be angled relative to the ground, as shown in FIG. 1, for example.

Furthermore, in some embodiments, the patient device support 72 and/or the healthcare device support 76 may be disposed on a top surface 74 of the main housing 70, as shown in FIGS. 1, 2A and 2B. For example, the patient device support 72 and/or the healthcare device support 76 may be disposed on or extend from the top surface 74 of the main housing 70 such that the main housing 70, the device supports 72, 76 and the devices 20, 40 combine to form a unit or an apparatus 10 that can be placed or moved into an environment, such as a healthcare and/or pharmaceutical environment, to provide translation services, as disclosed herein. More in particular, the apparatus or unit 10 can be disposed on a tabletop, countertop, or other location with the patient side (e.g., the patient device 20) easily accessible by the patient 21 and the healthcare side (e.g., the healthcare device 40) easily accessible by the healthcare provider or personnel 41.

In some cases, the main housing 70 (along with the device 20, 40 and supports 72, 76) may be supported on a movable or transportable cart or other like device. In particular, the cart or support structure 80 may include a tabletop or other like surface 82 upon which the main housing 70 and devices 20, 40 can be supported, with one or more wheels 85 disposed on bottom ends of one or more legs 84 or other like structures extending down from surface 82. In this manner, the entire unit or apparatus 10 can be easily transported from one location to another in order to provide translation services in different locations. This can be particularly beneficial in hospital or office setting, thereby allowing a healthcare provider to easily roll or transport the apparatus 100 into and out of patient rooms or other locations, as necessary.

Referring now to the high-level flow chart of FIG. 3, the method 200 of at least one embodiment is shown. In particular, the method 200 can begin and/or a communication session can be initiated from either the patient-side (e.g., though the patient device 20) or the healthcare-side (e.g., through the healthcare device 40) of the apparatus 10.

For instance, with reference to block 202, the patient can initiate a communication session by engaging with the patient device 20 and choosing a language. As just an example, the patient device 20 may display a list or group of selectable items each representing a different language. The patient can begin by selecting the language he/she would like to use for the communication session. In some cases, the patient device 20 can automatically detect the patient's language upon receiving an input (e.g., text or voice input) using AI or other algorithms. In some cases, the patient device 20 may also include one or more sensors, such as a motion sensors, camera, etc. that can detect the presence of a patient or customer at or proximate to the patient device 20 and can initiate the communication session thereupon.

In any event, to continue with the communication session, as shown at block 204, the patient can communicate an input to the patient device 20, for example, by speaking into the microphone. In other embodiments, the patient may be able to type an input (e.g., using the touchscreen display, keyboard or other input device). In yet another embodiment, the patient device 20 may include a graphical interface that displays several common inquiries or inputs from which the patient can select.

Once the input is received by the patient device 20, the input is transmitted to the translation module 50 for translation into a target healthcare language, as shown at block 206. In some cases, the healthcare provider or personnel 41 may have already selected a desired healthcare language (e.g., through the healthcare device 40). If not, in some cases, a prompt may be displayed to the healthcare provider on the healthcare device 40 to select or define a language. In yet another embodiment, the healthcare language may be set as a default, for example, as English, such that it may not need to be selected or defined for each communication session.

Next, after the translation module 50 has translated the input from the patient to the defined or selected target healthcare language, the translated output is communicated to the healthcare device, as shown at block 208, where it can be output by one or more of the healthcare output components, e.g., display screen, speaker, etc. In other words, regardless of the form of the input (e.g., text or speech), the output can be text displayed on the screen or speech or audio from the speaker(s) of the healthcare device.

From the healthcare-side, with reference to block 201, the healthcare provider or personnel can initiate a communication session by engaging with the healthcare device 40 and, if a language is not set by default, or if a different language is desired, choosing a language. As just an example, the healthcare device 40 may display a list or group of selectable items each representing a different language. The healthcare provider can begin by selecting the language he/she would like to use for the communication session. In some cases, the healthcare device 40 can automatically detect the healthcare personnel's language upon receiving an input (e.g., text or voice input) using AI or other algorithms. In some cases, the healthcare device 40 may also include one or more sensors, such as a motion sensors, camera, etc. that can detect the presence of a healthcare provider or other user at or proximate to the healthcare device 40 and can initiate the communication session thereupon.

Next, as shown at block 203, the healthcare provider can communicate an input to the healthcare device 40, for example, by speaking into the microphone, typing on the keyboard, touchscreen display or other input device. In some embodiments, the healthcare device 40 may include a graphical interface that displays several common inquiries or inputs from which the healthcare provider or personnel can select.

Once the input is received by the healthcare device 20, the input is transmitted to the translation module 50 for translation into a target patient language, as shown at block 205. In some cases, the patient 21 may have already selected a desired patient language (e.g., through the patient device 20). If not, in some cases, a prompt may be displayed to the patient on the patient device 20 to select or define a language.

Next, after the translation module 50 has translated the input from the healthcare provider to the defined or selected target patient language, the translated output is communicated to the patient device, as shown at block 207, where it can be output by one or more of the patient output components, e.g., display screen, speaker, etc. In other words, regardless of the form of the input (e.g., text or speech), the output can be text displayed on the screen or speech or audio from the speaker(s) of the patient device.

The communication session between the patient device 20 and the healthcare device 40 may continue back-and-forth with the patient and/or healthcare provider providing inputs to the respective devices 20, 40, translating the inputs, and communicating the translations to the other device 40, 20.

When the communication session is complete, for example, when the patient and the healthcare provider are done communicating with one another, the communication session can end or be terminated, as shown at block 210. This can occur in several different ways. For example, in some cases, the patient may terminate the session by selecting a corresponding button or option on the patient device. In other cases, the healthcare provider may terminate the session by selecting a corresponding button or option on the healthcare device. In yet another case, the system 100 or method 200 may be configured to automatically terminate the communication session upon the occurrence of an event. The event may be a timeout, which may occur when there is no activity (e.g., no inputs are being received and/or no action or activity on either device) for a predefined period of time.

Still referring to FIG. 3, in at least one embodiment, at the conclusion of the session, for example, after the session has been terminated, the patient may opt to receive a transcript of the communication session, as shown at block 212. Accordingly, in at least one embodiment, the apparatus may include a printer, generally referenced as 78 in FIG. 1. The printer 78 may be disposed within the main housing 70 and in communication with the control device 30. In some cases, a hole or slit 79 may be formed in the housing 70, for example, at or near the patient device 20, through which a printed transcript of the communication session may be fed. The patient can then remove the printed transcript of the communication session and maintain it for his/her records.

In other cases, the patient may opt for an electronic communication of the transcript of the communication session, for example, via e-mail, text or SMS message, etc.

Furthermore, still referring to the flow chart of FIG. 3, as shown at block 214, after termination of the communication session, in at least one embodiment, the method 200 will delete, e.g., permanently, at least some, and in some cases, any and all data corresponding to the communication session, including, for example, the inputs provided by the patient device 20 and/or healthcare device 40, the translations generated by the translation module 50, and in some cases, any patient-identifying information, including the patient's name, photos, voice, images, etc., from the apparatus 10 and system 100. More specifically, during the course of the communication session, certain information or data may be temporarily saved, e.g., input(s) provided by the patient and received by the patient device 20, input(s) provided by the healthcare provider and received by the healthcare device 40, translations generated by the translation module 50, identifications or names of medications, diagnoses, recommendations, instructions, etc., and in some cases, identifying information that may identify the patient, such as name, patient ID, etc. In some embodiments, all of that information will be deleted at the end of the communication session, in compliance with any healthcare regulations or laws, including but not limited to the Health Insurance Portability and Accountability Act (HIPPA).

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention. This written description provides an illustrative explanation and/or account of the present invention. It may be possible to deliver equivalent benefits using variations of the specific embodiments, without departing from the inventive concept. This description and these drawings, therefore, are to be regarded as illustrative and not restrictive.

The invention claimed is:

1. A method for two-way language translation in a healthcare environment, the method comprising:
   providing a healthcare translation apparatus comprising a single, standalone housing unit with a patient device and a healthcare device each mounted thereto, the patient device comprising at least one patient input component and at least one patient output component, the healthcare device comprising at least one healthcare input component and at least one healthcare output component;
   defining the healthcare translation apparatus as further comprising a translation module configured to translate a patient input in a patient language to a healthcare output in a healthcare language, and to translate a healthcare input in the healthcare language to a patient output in the patient language;
   initiating a communication session at the healthcare translation apparatus;
   receiving, by at least one of the patient device or the healthcare device, an input in an input language, the input language being one of the patient language or the healthcare language;
   translating, in real-time, via at least one processor and the translation module, the input into an output in an output language, the output language being one of the patient language or the healthcare language;
   communicating the output to the other one of the patient device or the healthcare device;
   terminating the communication session at the healthcare translation apparatus; and
   upon termination of the communication session, deleting all data corresponding to the patient input, healthcare input, patient output and healthcare output.

2. The method as recited in claim 1 further comprising defining the at least one patient input as comprising a microphone capable of receiving spoken audio as the patient input.

3. The method as recited in claim 2 further comprising defining the at least one healthcare input as comprising a microphone capable of receiving spoken audio as the healthcare input and a keyboard capable of receiving typed text as the healthcare input.

4. The method as recited in claim 1 further comprising defining the single, standalone housing unit as comprising an interior portion within which at least one control device is disposed, the at least one control device being in localized communication with the patient device and the healthcare device and comprising at least one computer processor, at least one memory, at least one storage device, and at least one communication device.

5. The method as recited in claim 4 further comprising defining the healthcare translation apparatus as further comprising a patient device support, the patient device support comprising at least one angled surface upon which the at least one patient input component and the at least one patient output component are disposed.

6. The method as recited in claim 5 further comprising defining the healthcare translation apparatus as further comprising a healthcare device support, the healthcare device support comprising at least one angled surface upon which the at least one healthcare input component and the at least one healthcare output component are disposed.

7. The method as recited in claim 6 wherein the patient device support and the healthcare device support are disposed on a top surface of the single, standalone housing unit.

8. The method as recited in claim 5 further comprising printing a transcript of the communication session via a printer disposed within the single, standalone housing unit.

9. A healthcare translation apparatus for two-way language translation in a healthcare environment, said apparatus comprising:
   a transportable main housing;
   a patient device mounted to said transportable main housing, said patient device comprising at least one patient input component and at least one patient output component;
   a healthcare device mounted to said transportable main housing, said healthcare device comprising at least one healthcare input component and at least one healthcare output component;
   a translation module configured to translate a patient input in a patient language to a healthcare output in a healthcare language, and to translate a healthcare input in the healthcare language to a patient output in the patient language;
   wherein a patient input is received by the patient device, translated in real-time via the translation module into the healthcare output, and transmitted to the healthcare device for output by the at least one healthcare output component;
   wherein a healthcare input is received by the healthcare device, translated in real-time via the translation module into the patient output, and transmitted to the patient device for output by the at least one patient output component;
   wherein, at an end of a communication session between the patient device and the healthcare device, all data corresponding to the patient input, healthcare input, patient output or healthcare output is deleted; and
   wherein said transportable main housing comprises a plurality of wheels for selective movement of said transportable main housing and said patient device and said healthcare device mounted thereto.

10. The apparatus as recited in claim 9 wherein the at least one patient input component comprises at least one microphone capable of receiving spoken audio as the patient input.

11. The apparatus as recited in claim 10 wherein the at least one healthcare input component comprises at least one microphone capable of receiving spoken audio as the healthcare input, and a keyboard capable of receiving typed text as the healthcare input.

12. The apparatus as recited in claim 9 wherein said transportable main housing defines an interior portion within which at least one control device is disposed, the at least one control device being in localized communication with the patient device and the healthcare device, and comprising at least one computer processor, at least one memory, at least one storage device and at least one communication device.

13. The apparatus as recited in claim 12 further comprising at least one patient device support upon which at least a portion of the patient device is disposed.

14. The apparatus as recited in claim 13 wherein the at least one patient device support comprises an angled surface upon which at least a portion of the patient device is disposed.

15. The apparatus as recited in claim 13 further comprising at least one healthcare device support upon which at least a portion of the healthcare device is disposed.

16. The apparatus as recited in claim 14 wherein the at least one healthcare device support comprises an angled surface upon which at least a portion of the healthcare device is disposed.

17. The apparatus as recited in claim 12 further comprising a printer disposed within the transportable main housing, the printer being capable of printing a transcript of the communication session.

18. A translation apparatus for two-way language translation, said apparatus comprising:
a transportable main housing;
a patient device mounted to said transportable main housing, said patient device comprising at least one patient input component and at least one patient output component;
a healthcare device mounted to said transportable main housing, said healthcare device comprising at least one healthcare input component and at least one healthcare output component;
a translation module configured to translate a patient input in a patient language to a healthcare output in a healthcare language, and to translate a healthcare input in the healthcare language to a patient output in the patient language;
wherein a patient input is received by the patient device, translated in real-time via the translation module into the healthcare output, and transmitted to the healthcare device for output by the at least one healthcare output component;
wherein a healthcare input is received by the healthcare device, translated in real-time via the translation module into the patient output, and transmitted to the patient device for output by the at least one patient output component;
wherein all of said patient input, said healthcare input, said patient output, said healthcare output and said translations are maintained locally, on the healthcare translation apparatus, and
wherein said transportable main housing comprises a plurality of wheels for selective movement of said transportable main housing and said patient device and said healthcare device mounted thereto.

* * * * *